United States Patent
Chang et al.

(10) Patent No.: US 11,754,485 B2
(45) Date of Patent: Sep. 12, 2023

(54) VALIDATION TEST PIECE FOR VALIDATING BIO-SAMPLE DETECTION DEVICE AND METHOD OF VALIDATING THE BIO-SAMPLE DETECTION DEVICE

(71) Applicant: BONRAYBIO CO., LTD., Taichung (TW)

(72) Inventors: Chih-Pin Chang, Taichung (TW); Hsi-Wen Huang, Taichung (TW)

(73) Assignee: Bonraybio Co., Ltd., Taichung (TW)

( * ) Notice: Subject to any disclaimer, the term of this patent is extended or adjusted under 35 U.S.C. 154(b) by 281 days.

(21) Appl. No.: 17/180,024

(22) Filed: Feb. 19, 2021

(65) Prior Publication Data

US 2021/0293688 A1 Sep. 23, 2021

(30) Foreign Application Priority Data

Mar. 19, 2020 (TW) .................................. 109109244

(51) Int. Cl.
*G01N 15/06* (2006.01)
*G01N 33/487* (2006.01)

(52) U.S. Cl.
CPC .......... *G01N 15/06* (2013.01); *G01N 33/487* (2013.01); *G01N 2015/0693* (2013.01)

(58) Field of Classification Search
CPC .................. G01N 15/06; G01N 33/487; G01N 2035/00148; G01N 2035/00138; G02B 21/34; B01L 3/00; B01L 3/5055; B01L 2300/0825

See application file for complete search history.

(56) References Cited

U.S. PATENT DOCUMENTS

| | | | |
|---|---|---|---|
| 2005/0237607 A1 | 10/2005 | Tenny | |
| 2009/0011425 A1* | 1/2009 | Delaage | G01N 1/312 435/7.1 |
| 2011/0211058 A1 | 9/2011 | McCollum et al. | |
| 2012/0123686 A1* | 5/2012 | Xiang | G01N 33/48792 702/19 |
| 2012/0314092 A1 | 12/2012 | Chu et al. | |

(Continued)

FOREIGN PATENT DOCUMENTS

| CA | 3039953 A1 * | 10/2019 | ............ B01L 3/5023 |
|---|---|---|---|
| CN | 100342973 C * | 10/2007 | .............. B01L 3/508 |

(Continued)

OTHER PUBLICATIONS

Search Report appended to an Office Action, which was issued to Taiwanese counterpart application No. 109109244 by the TIPO dated Apr. 2021.

*Primary Examiner* — Maurice C Smith
(74) *Attorney, Agent, or Firm* — Rosenberg, Klein & Lee

(57) ABSTRACT

A validation test piece is for validating a bio-sample detection device, which includes an insert port for insertion of the validation test piece and a detection module. The validation test piece includes a base seat, a test element, a standardized data and a top cover. The base seat includes a seat body and a receiving member disposed on the seat body. The test element is connected to the receiving member, and includes a test region to be detected by the detection module. The standardized data corresponds to a sample number of the test region. The top cover is connected to the base seat for covering the test element.

19 Claims, 10 Drawing Sheets

(56) References Cited

U.S. PATENT DOCUMENTS

2020/0078781 A1\* 3/2020 Beckley ................... B01L 3/50
2020/0114348 A1\* 4/2020 Laverack .............. B01L 3/5023

FOREIGN PATENT DOCUMENTS

| EP | 3244250 A1 \* | 11/2017 | ......... A61B 5/14507 |
| TW | 201514861 A | 4/2015 | |
| TW | M502845 U | 6/2015 | |
| WO | WO-2019048018 A1 \* | 3/2019 | ......... A61B 10/0058 |

\* cited by examiner

VALIDATION TEST PIECE FOR VALIDATING BIO-SAMPLE DETECTION DEVICE AND METHOD OF VALIDATING THE BIO-SAMPLE DETECTION DEVICE

CROSS-REFERENCE TO RELATED APPLICATION

This application claims priority of Taiwan Patent Application No. 109109244, filed on Mar. 19, 2020.

FIELD

The disclosure relates to a validation mechanism, and more particularly to a validation test piece for validating a bio-sample detection device and a method of validating the bio-sample detection device.

BACKGROUND

Sperm quality test is an effective way of diagnosing causes of infertility. Conventionally, the to-be-tested semen is dripped onto a test piece, followed by measuring the test piece using a bio-sample detection device for testing the semen sample like sperm count, etc. Precision of the bio-sample detection device would directly affect the test result, and validation of the bio-sample detection device is therefore an important step prior to sample test. A test solution is commonly used for validating the bio-sample detection device. Specifically, the test solution simulates the concentration of the sperm in the semen, and a standard concentration is labeled on the container of the test solution. In validation, the test solution is dripped onto the test piece, followed by measuring the test piece using a bio-sample detection device. The measurement result is then compared with the standard concentration labeled on the container for determining whether the bio-sample detection device's measurement is accurate or not. However, the standard concentration of the test solution is often in a range, which makes it difficult to precisely validate the bio-sample detection device. In addition, the degree of uniformity of the test solution will also affect the validation results. Therefore, it is desirable in the art to improve the validation mechanism for the bio-sample detection device.

SUMMARY

Therefore, a first aspect of the disclosure is to provide a validation test piece that can alleviate at least one of the drawbacks of the prior art.

The validation test piece is adapted for validating a bio-sample detection device, which includes an insert port for insertion of the validation test piece and a detection module.

The validation test piece includes a base seat, a test element, a standardized data and a top cover. The base seat includes a seat body and a receiving member that is disposed on the seat body. The test element is connected to the receiving member, and includes a test region adapted to be detected by the detection module of the bio-sample detection device. The standardized data corresponds to a sample number of the test region of the test element. The top cover is connected to the base seat and covers the test element.

A second aspect of the disclosure is to provide a method of validating a bio-sample detection device, which includes an insert port and a detection module.

The method includes:
(a) preparing a validation test piece of the first aspect;
(b) inserting the validation test piece into the insert port of the bio-sample detection device such that the test region of the validation test piece corresponds in position to the detection module of the bio-sample detection device;
(c) operating the detection module to detect the test region of the test element to obtain a detection result; and
(d) comparing the detection result with the standardized data to validate the bio-sample detection device.

A third aspect of the disclosure is to provide a validation test piece that can alleviate at least one of the drawbacks of the prior art.

The validation test piece includes a base seat, a test element, a standardized data and a top cover.

The base seat includes a seat body and a receiving member that is disposed on the seat body. The test element is connected to the receiving member, and includes a test region. The test region includes a plurality of test portions that are spaced apart from one another, and a surrounding portion that cooperates with the test portions to occupy the test region. The standardized data indicates the number of the test potions. The top cover is connected to the base seat and covers the test element.

A fourth aspect of the disclosure is to provide a validation test piece that can alleviate at least one of the drawbacks of the prior art.

The validation test piece is adapted for validating a bio-sample detection device that includes an insert port for insertion of the validation test piece, and a detection module.

The validation test piece includes a base seat, a test element, a standardized data and a top cover.

The base seat includes a seat body and a receiving member that is disposed on the seat body. The test element is connected to the receiving member, and includes a test region that is adapted to be detected by the detection module of the bio-sample detection device. The test region includes a surrounding portion. The standardized data indicates a sample number in the surrounding portion of the test region of the test element. The top cover is connected to the base seat and covers the test element.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
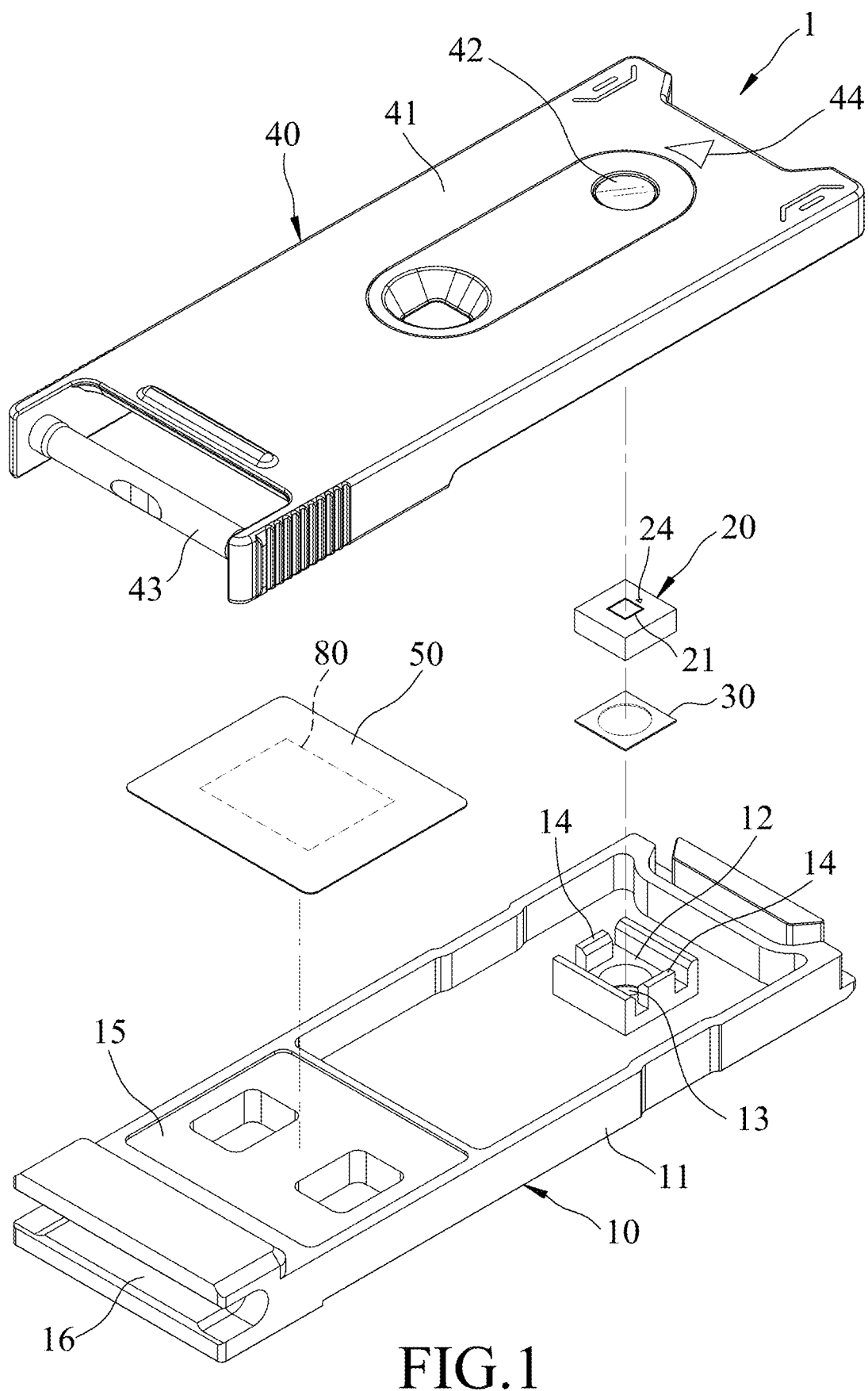
FIG. 1 is an exploded perspective view of an embodiment of a validation test piece according to the present disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 6:
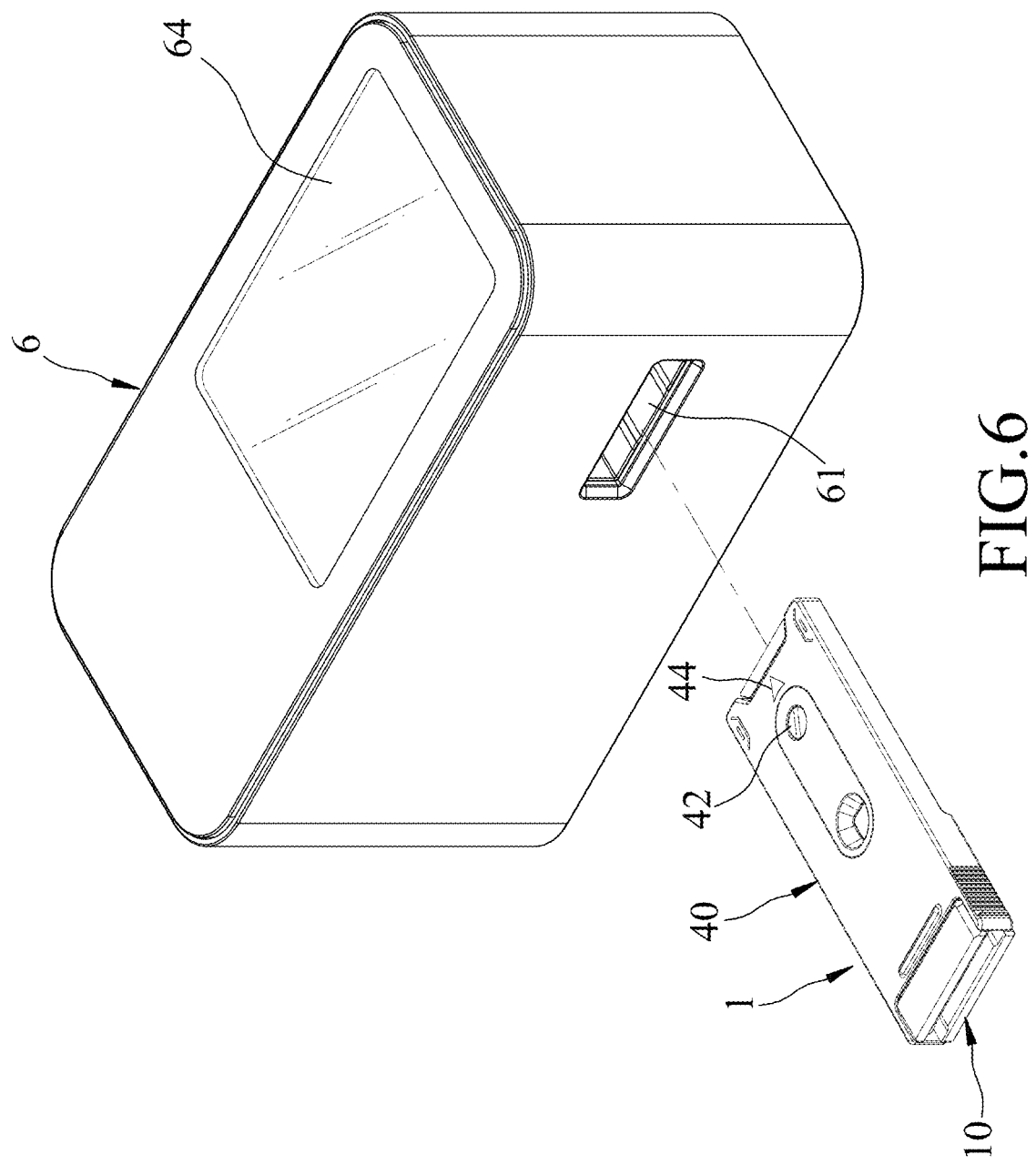
FIG. 6 is a perspective view, illustrating the embodiment to be inserted into an insert port of a bio-sample detection device.
Figure 7:
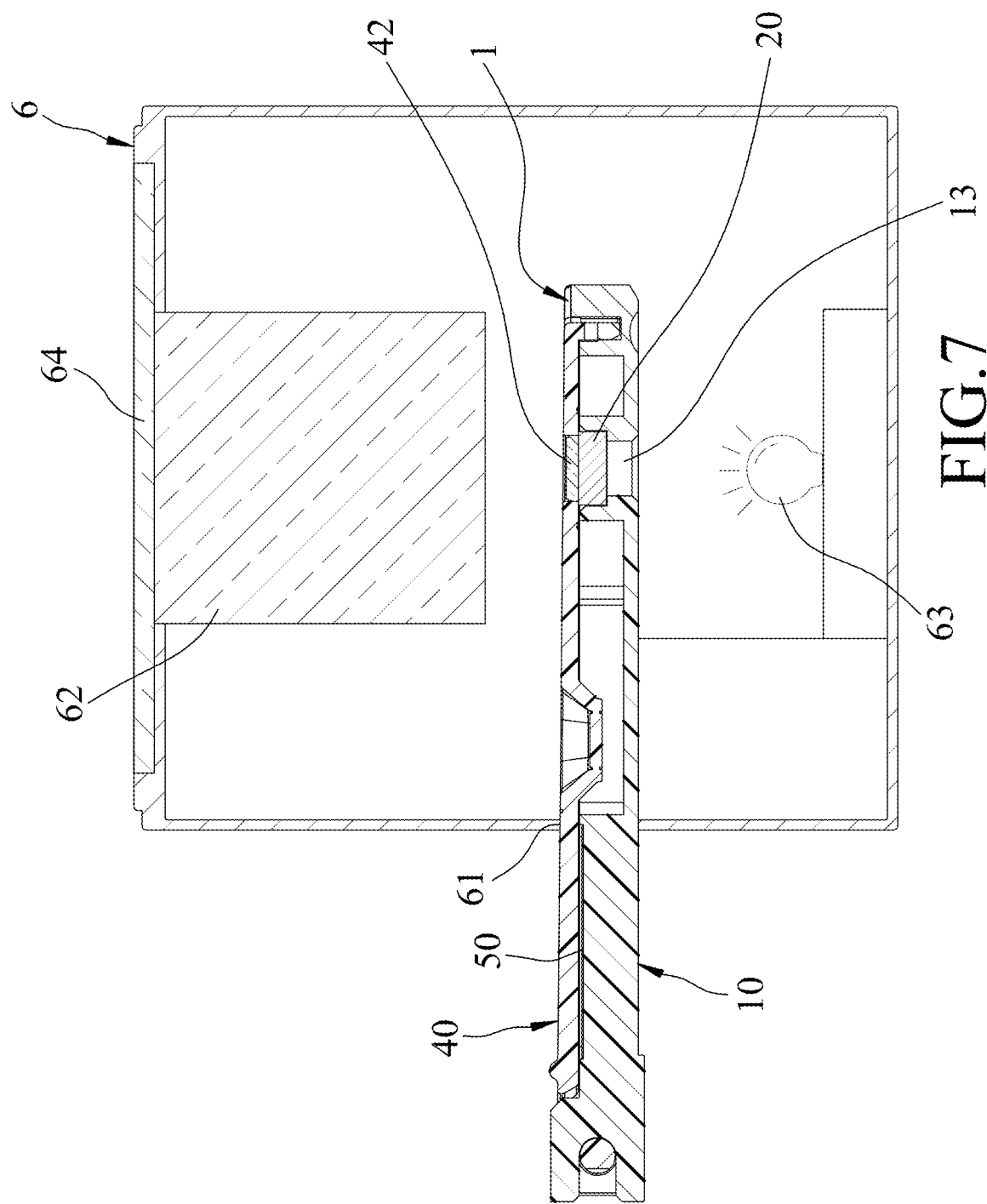
FIG. 7 is a sectional view taken when the embodiment is inserted into the insert port of the bio-sample detection device.

Referring to FIGS. 1, 6 and 7, an embodiment of a validation test piece 1 is adapted for validating a bio-sample detection device 6. The bio-sample detection device 6 includes an insert port 61 for insertion of the validation test piece 1, a detection module 62, a light source 63 and a display monitor 64. The validation test piece 1 includes a base seat 10, a test element 20, a standardized data 80, an adhesive 30, a top cover 40 and a label 50.

Referring further to FIGS. 1 to 5, the base seat 10 includes a seat body 11, a receiving member 12 that is disposed on the seat body 11, a through hole 13 that is formed in the seat body 11 and that communicates the receiving member 12, a plurality of clamp blocks 14 that are disposed on the seat body 11 for clamping the test element 20, a standard data display region 15 located on the seat body 11, and an engaging groove 16 that is formed in the seat body 11.

The test element 20 is disposed on the receiving member 12, and includes a test region 21 adapted to be illuminated by the light source 63 and detected by the detection module 62 of the bio-sample detection device 6. In some embodiments, the test element 20 is connected to the receiving member 12. The label 50 is attached to the standard data display region 15, and the standardized data 80 is shown on the label 50 and corresponds to a sample number of the test region 21 of the test element 20. In this embodiment, the test region 21 of the test element 20 includes a plurality of test portions 22 that are spaced apart from one another and that are adapted to be detected by the detection module 62 of the bio-sample detection device 6, a surrounding portion 23 that cooperates with the test portions 22 to occupy the test region 21, and a foolproof mark 24 that is located outside of the test region 21 so as to facilitate the test element 20 to be positioned relative to the receiving member 12 during assembly of the test element 20 to the base seat 10. In this embodiment, the standardized data 80 indicates the number of the test portions 22. The through hole 13 is adapted to be disposed between and aligned with the detection module 62 and the light source 63, and exposes the test region 21 of the test element 20 therein.

The test portions 22 and the surrounding portion 23 of the test element 20 may be formed by etching techniques. In this embodiment, the test element 20 is a photomask, the test portions 22 of the test element are light-transmissible and evenly distributed in the test region 21, and the surrounding portion 23 of the test element 20 is opaque. It should be noted that the number and distribution of the test portions 22 may be changed according to practical requirements. FIG. 3 shows a variation of the test element 20, in which the sizes of the test portions 22 are smaller and the number of test portions 22 is greater, compared to those of FIG. 2. The density of the test portions 22 of the test element 20 may correspond to a concentration of a to-be-tested sample (not shown). Therefore, the test element 20 of the validation test piece 1 can be used for validating the bio-sample detection device 6 for optimizing subsequent measurement of the to-be-tested sample.

The test element 20 may be made of quartz or soda-lime glass, and may have a volume not greater than 200 mm$^3$. In this embodiment, the test element 20 has a dimension of 6 mm*6 mm*2.3 mm. The test portions 22 of the test element 20 have a density that ranges from 1 to 500,000 per square centimeter. In certain embodiments, the density may be 25,000 per square centimeter or 50,000 per square centimeter, and each of the test portions 22 has a diameter ranging from 1 μm to 10 μm, such as 5 μm.

The adhesive 30 is connected between the receiving member 12 and the test element 20 for adhering the test element 20 to the receiving member 12. In this embodiment, the adhesive 30 may be a UV curable adhesive.

Besides adhering the test element 20 to the receiving member 12 via the adhesive 30, the clamp blocks 14 are also another mechanism for connecting the test element 20 to the receiving member 12. In this embodiment, both the adhesive 30 and the clamp blocks 14 are utilized to ensure that the test element 20 is securely connected to the receiving member 12. In certain embodiments, other fixing mechanisms, such as a ring-shaped double sided tape, can be used for fixing the test element 20 to the receiving member 12.

The top cover 40 is connected to the base seat 10, and is adapted for covering the test element 20. In this embodiment, the top cover 40 includes a cover body 41, a light-transmissible window 42, a pivot rod 43 and an inserting direction indicator 44. The light-transmissible window 42 is disposed on the cover body 41 and corresponds in position to the test region 21 of the test element 20 when the top cover 40 covers the base seat 10, thereby allowing the detection module 62 of the bio-sample detection device 6 to detect the test region 21. The pivot rod 43 is rotatably engaged with the engaging groove 16 of the base seat 10, such that the top cover 40 is pivotable relative to the base seat 10. The inserting direction indicator 44 is disposed on the cover body 41, and represents the direction in which the validation test piece 1 is inserted into the insert port 61 in the bio-sample detection device 6.

The label 50 may be attached to the top cover 40 instead of the standard data display region 15. In certain embodiments, the label 50 may be omitted, and the standardized data 80 may be shown on the base seat or the top cover 40.

Referring to FIGS. 1, 2, 4-7 and 10, a method of validating the bio-sample detection device 6 using the embodiment of the validation test piece 1 is disclosed. The method includes steps (A) to (D).

In step (A), the validation test piece 1 is prepared.

In step (B), the validation test piece 1 is inserted into the insert port 61 of the bio-sample detection device 6 such that the light-transmissible window 42 of the top cover 40 and the test region 21 of the test element 20 are aligned with the test module 62, and the test region 21 of the validation test piece 1 is illuminated by the light source 63.

In step (C), the detection module 62 is operated to detect the test region 21 of the test element 20 to obtain a detection result. In other words, the detection module 62 is operated to detect the number of the test portions 22 of the test element 20 to obtain the detection result. In this embodiment, the detection module 62 includes a detector, a lens and an amplifier (not shown), and is capable of detecting the number of the test portions 22 of the test region 21 and the sample number of the to-be-tested sample. In this embodiment, the light source 63 may be a UV light that can cure the UV curable adhesive, and can illuminate the test element 20 through the through hole 13 for improving quality of detection of the bio-sample detection device 6. The detection result may be displayed by the display monitor 64 to be viewed by a user of the bio-sample detection device 6.

In step (D), the detection result is compared with the standardized data 80 to validate the bio-sample detection device 6.

Figure 8:
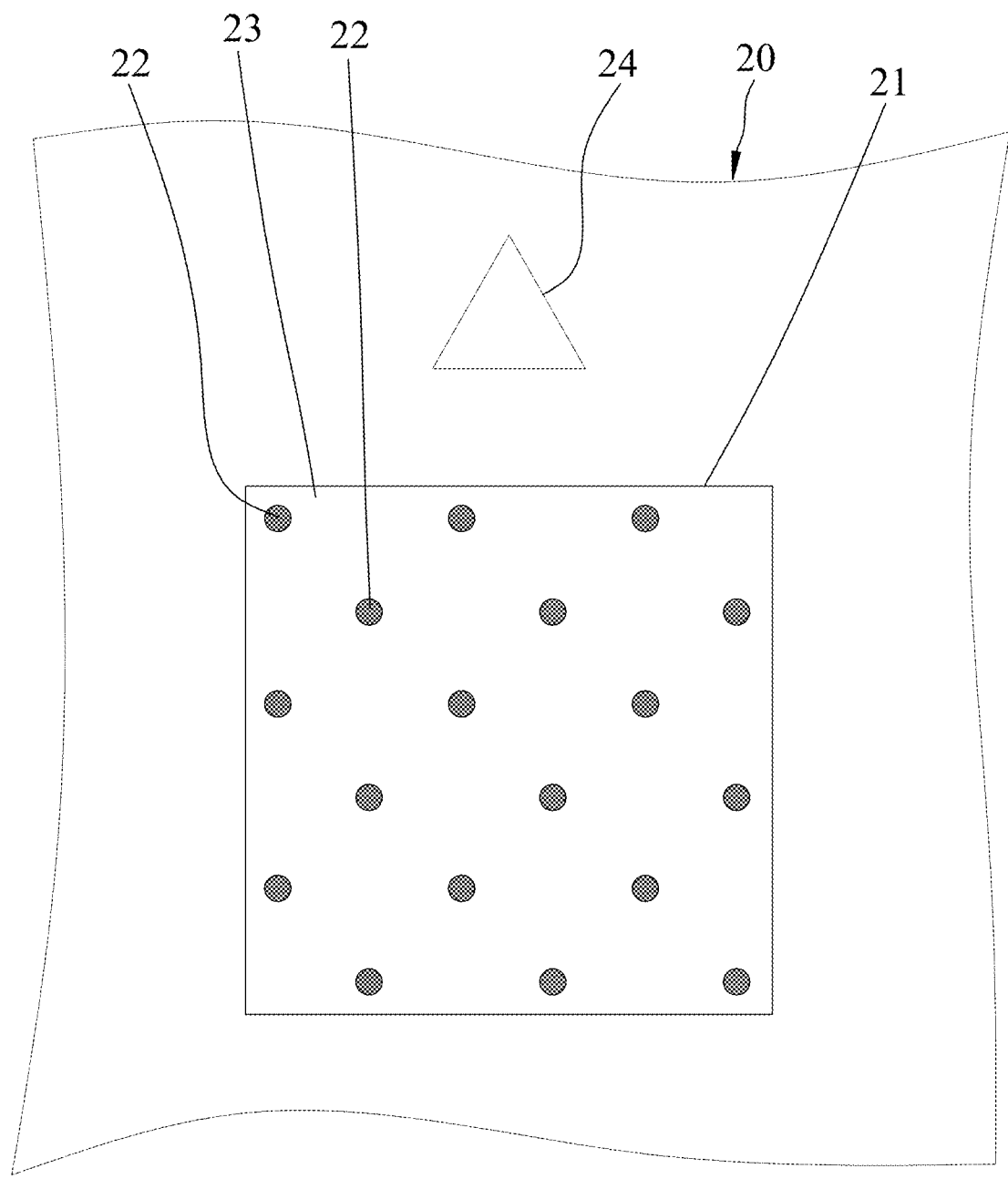
FIG. 8 is a fragmentary top view of another variation of the test element of the embodiment.

Referring to FIG. 8, in another variation of the test element 20, the test portions 22 are opaque, and the surrounding portion 23 is light-transmissible. The validation of the bio-sample detection device 6 can still be achieved by using such test element 20.

Figure 2:
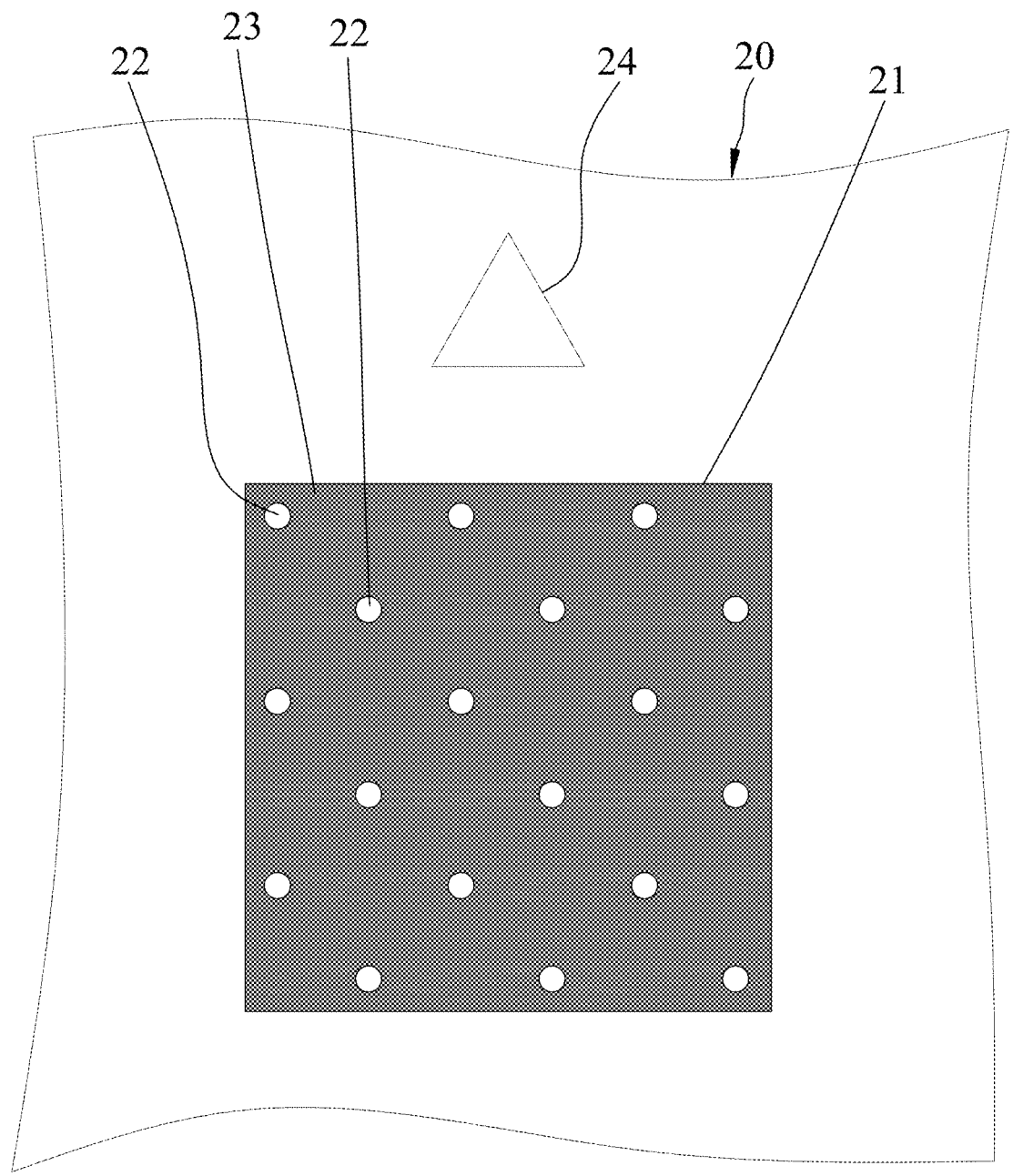
FIG. 2 is a fragmentary top view of a test element of the embodiment.
Figure 3:
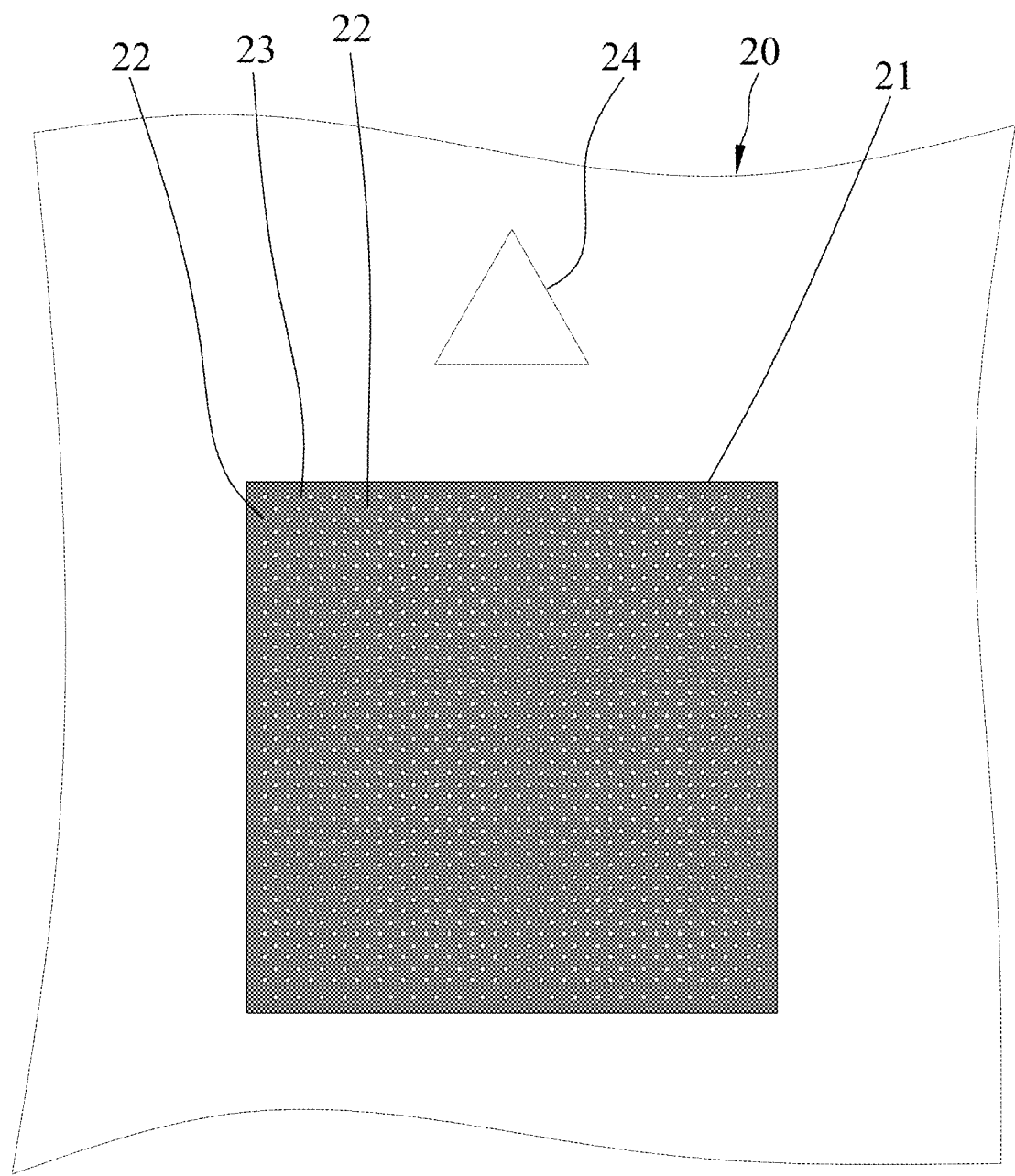
FIG. 3 is a fragmentary top view of a variation of the test element of the embodiment.
Figure 4:
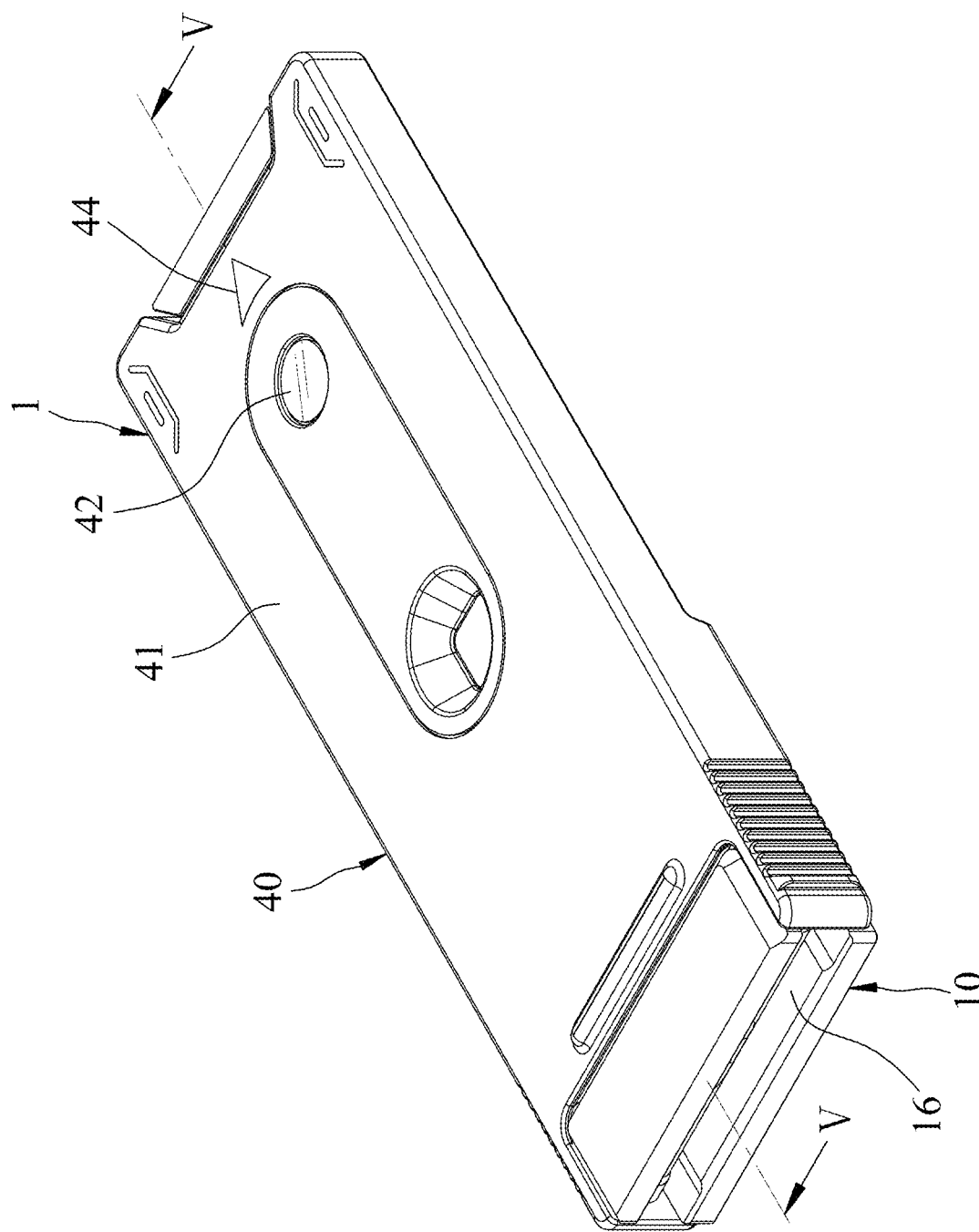
FIG. 4 is a perspective view of the embodiment.
Figure 5:
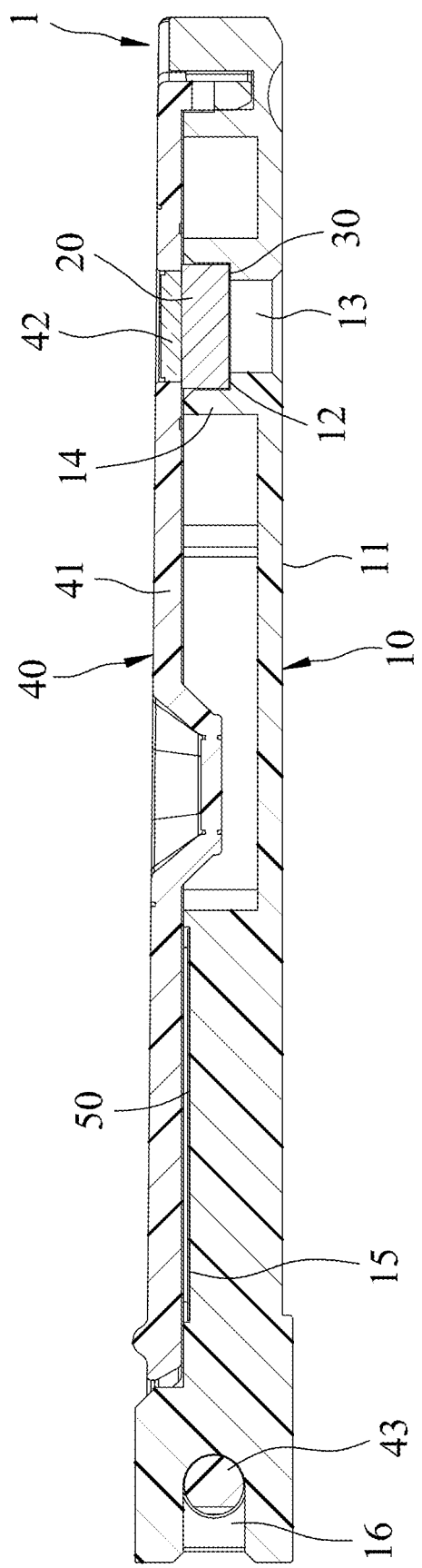
FIG. 5 is a sectional view of the embodiment, taken along line V-V of FIG. 4.
Figure 9:
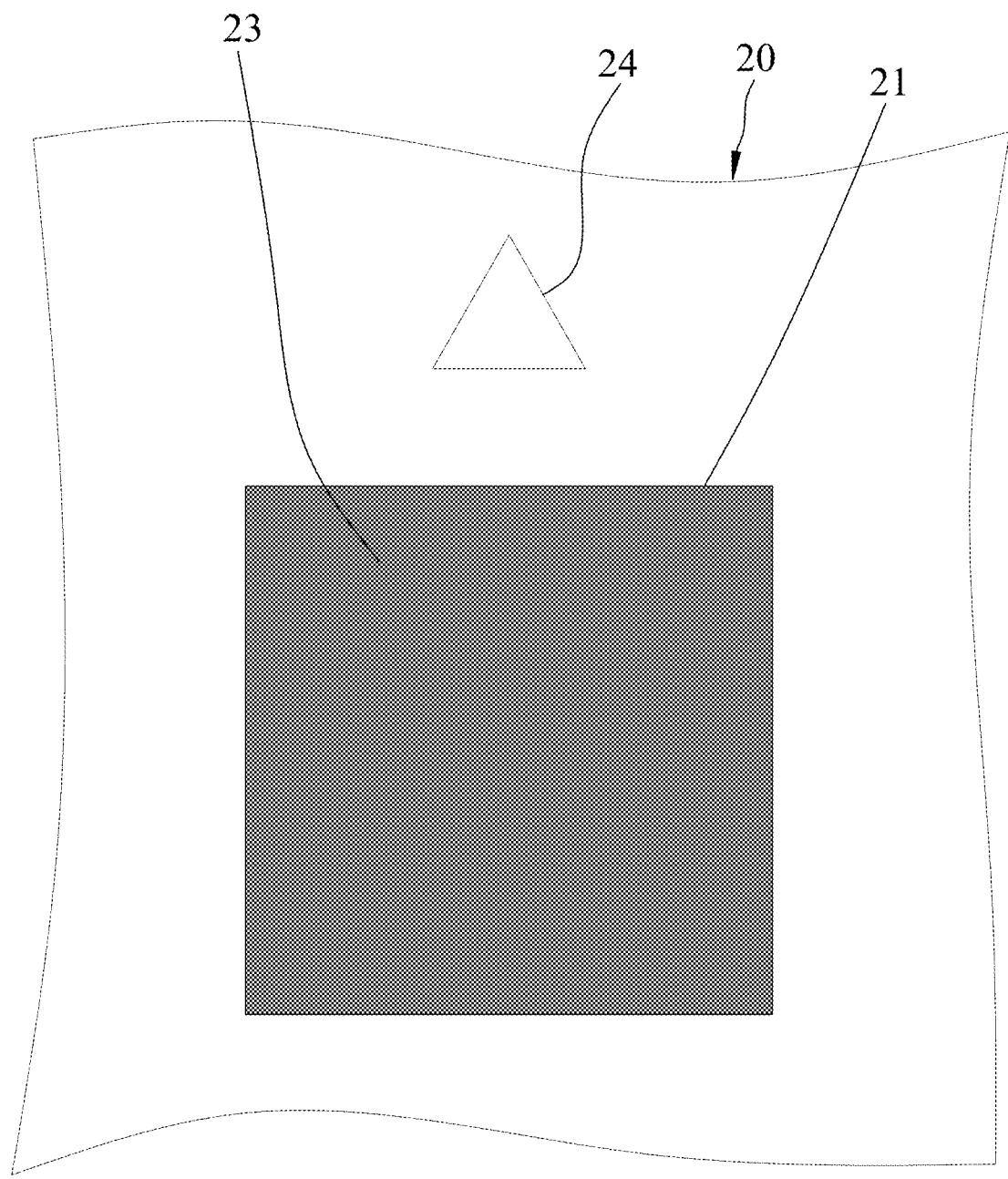
FIG. 9 is a fragmentary top view of yet another variation of the test element of the embodiment.
Figure 10:
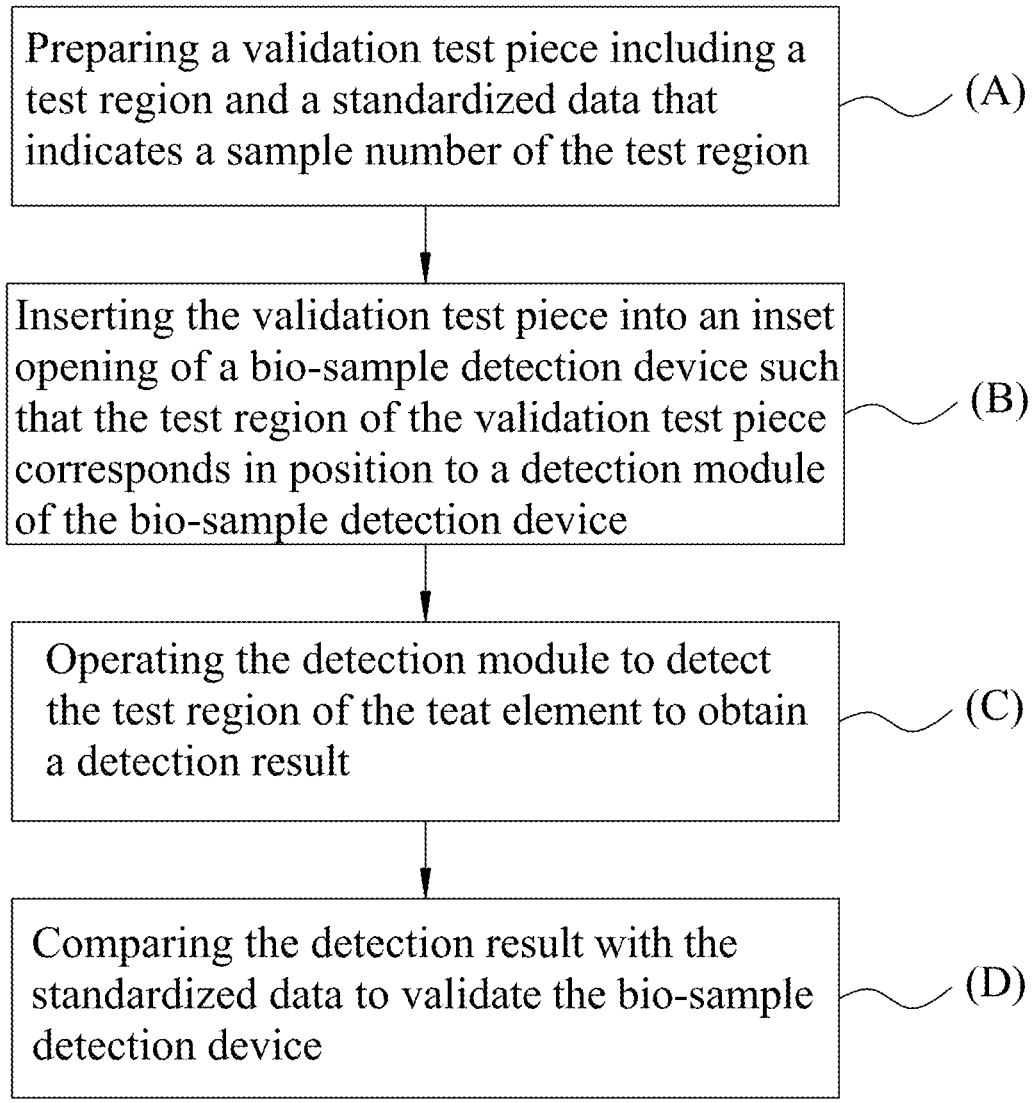
FIG. 10 is a flow chart of a method of validating the bio-sample detection device using the validation test piece according to the present disclosure.

Referring to FIG. 9, in yet another variation of the test element 20, the test region 21 of the test element only includes the surrounding portion 23 and does not include the test portions 22 (see FIG. 2). Referring further to FIG. 1, the standardized data 80 may indicate a sample number in the surrounding portion 23 of the test region 21 of the test element 20. In this embodiment, since the test region 21 does not include the test portions 22, the standardized data 80 may indicate that the sample number is zero. In practical application of such test element 20, when the detection result of the bio-sample detection device 6 is zero, which is consistant with the standardized data 80, the bio-sample detection device 6 is successfully validated. When the detection result of the bio-sample detection device 6 is not zero, which is inconsistent with the standardized data 80, the display monitor 64 of the bio-sample detection device 6 may display an error message, and the user may check the bio-sample detection device 6 for possible errors.

To sum up, the validation test piece 1 according to the present disclosure provides a precise standardized data 80 for validation of the bio-sample detection device 6. Compared with the conventional test solution that has a concentration range and may be a non-uniform solution, the number of test portions 22 of the test element 20 is fixed and the test portions 22 are evenly distributed in the test region 21, leading to more precise validation result. The test element 20 of this disclosure may be made by precise etching techniques, which is also beneficial for obtaining a precise validation result.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiment but is intended to cover various arrangements included within the spirit and scope of the broadest interpretation so as to encompass all such modifications and equivalent arrangements.

What is claimed is:

1. A validation test piece adapted for validating a bio-sample detection device, the bio-sample detection device including an insert port for insertion of said validation test piece and a detection module, said validation test piece comprising:
    a base seat including a seat body and a receiving member that is disposed on said seat body;
    a test element connected to said receiving member, and including a test region adapted to be detected by the detection module of the bio-sample detection device, said test region including a plurality of test portions that are spaced apart from one another and that are adapted to be detected by the detection module of the bio-sample detection device, and a surrounding portion that cooperates with said plurality of test portions to occupy said test region;
    a standardized data that corresponds to a sample number of said test region of said test element, said standardized data indicates the number of said test portions; and
    a top cover connected to said base seat and covering said test element.

2. The validation test piece as claimed in claim 1, wherein:
    said test portions of said test element are light-transmissible; and
    said surrounding portion of said test element is opaque.

3. The validation test piece as claimed in claim 1, wherein:
    said test portions of said test element are opaque; and
    said surrounding portion of said test element is light-transmissible.

4. The validation test piece as claimed in claim 1, wherein said base seat further includes a plurality of clamp blocks that are disposed on said seat body for clamping said test element.

5. The validation test piece as claimed in claim 1, wherein said seat body of said base seat is formed with a through hole that is adapted to be disposed between and aligned with the detection module and the light source and that exposes said test region of said test element.

6. The validation test piece as claimed in claim 1, wherein said top cover includes a cover body and a light-transmissible window that corresponds in position to said test region of said test element, thereby allowing the detection module of the bio-sample detection device to detect said test region.

7. The validation test piece as claimed in claim 1, further comprising an adhesive that is connected between said receiving member and said test element for adhering said test element to said receiving member.

8. The validation test piece as claimed in claim 1, wherein said test element further includes a foolproof mark that is located outside of said test region so as to facilitate said test element to be positioned relative to said receiving member during assembly of said test element to said base seat.

9. The validation test piece as claimed in claim 1, wherein:
    said base seat further includes a standard data display region located on said seat body;
    said validation test piece further comprises a label that is attached to said standard data display region; and
    said standardized data is shown on said label.

10. The validation test piece as claimed in claim 1, wherein:
    said base seat further includes an engaging groove that is formed in said seat body; and said top cover includes a pivot rod that is rotatably engaged with said engaging groove of said base seat, such that said top cover is pivotable relative to said base seat.

11. The validation test piece as claimed in claim 1, wherein said top cover includes an inserting direction indicator that represents the direction in which said validation test piece is inserted into the insert port of the bio-sample detection device.

12. The validation test piece as claimed in claim 1, wherein said test element is a photomask and made of one of quartz and soda-lime glass.

13. The validation test piece as claimed in claim 1, wherein a volume of said test element is not greater than 200 mm$^3$.

14. The validation test piece as claimed in claim 1, wherein said test portions of said test element have a density that ranges from 1 to 500,000 per square centimeter.

15. The validation test piece as claimed in claim 1, wherein a diameter of each of said test portions of said test element ranges from 1 μm to 10 μm.

16. A method of validating a bio-sample detection device, the bio-sample detection device including an insert port and a detection module, the method comprising:
(A) preparing a validation test piece of claim 1;
(B) inserting the validation test piece into the insert port of the bio-sample detection device such that the test region of the validation test piece corresponds in position to the detection module of the bio-sample detection device;
(C) operating the detection module to detect the test region of the test element to obtain a detection result; and
(D) comparing the detection result with the standardized data to validate the bio-sample detection device.

17. The method as claimed in claim 16, wherein:
in step (A), the test region of the validation test piece includes a plurality of spaced-apart test portions and a surrounding portion cooperating the test portions to occupy the test region, and the standardized data corresponds to the number of the test portions; and
in step (C), the detection module is operated to detect the number of the test portions to obtain the detection result.

18. A validation test piece comprising:
a base seat including a seat body and a receiving member that is disposed on said seat body;
a test element connected to said receiving member, and including a test region, said test region including a plurality of test portions that are spaced apart from one another and a surrounding portion that cooperates with said test portions to occupy said test region;
a standardized data that indicated the number of said test portions; and
a top cover being connected to said base seat and covering said test element.

19. A validation test piece adapted for validating a bio-sample detection device including an insert port for insertion of said validation test piece and a detection module, said validation test piece comprising:
a base seat including a seat body and a receiving member that is disposed on said seat body;
a test element connected to said receiving member, and including a test region adapted to be detected by the detection module of the bio-sample detection device, said test region being consisting of a surrounding portion;
a standardized data indicating a sample number in said surrounding portion of said test region of said test element; and
a top cover connected to said base seat and covering said test element.

* * * * *